United States Patent [19]

McKown et al.

[11] Patent Number: 5,305,760

[45] Date of Patent: Apr. 26, 1994

[54] METHOD FOR REJECTING ELECTRICAL INTERFERENCE FROM PHYSIOLOGICAL MEASUREMENTS

[75] Inventors: Russell C. McKown, Dallas; Chris Eckert, Lewisville; Michael D. Quinn, Plano, all of Tex.

[73] Assignee: Interflo Medical Inc., Plano, Tex.

[21] Appl. No.: 832,410

[22] Filed: Feb. 7, 1992

[51] Int. Cl.$^5$ ............................................. A61B 5/021
[52] U.S. Cl. ...................................... 128/692; 128/713
[58] Field of Search ............... 128/713, 691, 692, 670; 73/861.06, 204.16, 204.17, 204.18, 204.19, 204.23

[56] References Cited

U.S. PATENT DOCUMENTS

| | | | |
|---|---|---|---|
| 3,485,099 | 12/1969 | Collins | 73/204.17 |
| 4,236,527 | 12/1980 | Newbower et al. | 128/692 |
| 4,507,974 | 4/1985 | Yelderman | 73/861.06 |
| 4,537,200 | 8/1985 | Widrow | 128/696 |
| 4,967,753 | 11/1990 | Haase et al. | 128/772 |
| 5,046,505 | 9/1991 | Sekii et al. | 128/713 |
| 5,074,310 | 12/1991 | Mick | 128/774 |
| 5,080,106 | 1/1992 | Sekii et al. | 128/691 |
| 5,174,293 | 12/1992 | Hagiwara | 128/908 |

FOREIGN PATENT DOCUMENTS

WO84/03219  8/1984  European Pat. Off.
0126931   12/1984  European Pat. Off.

OTHER PUBLICATIONS

Yelderman, "Continuous Measurement of Cardiac Output With the Use of Stochastic System Identification Techniques", *J Clin Monit* 1990; 6(4):322-332.

"Datenerfassungs-Chip ersetzt 30 Standard-ICs", by McGlinchey et al., *Elektronik*, vol. 39, No. 13, Jun. 22, 1990, pp. 90-93.

Primary Examiner—Lee S. Cohen
Assistant Examiner—Samuel Gilbert
Attorney, Agent, or Firm—Bruce M. Canter; Michael D. Stein

[57] ABSTRACT

Methods and apparatus for eliminating the effects of electrosurgical interference on continuous, heat-based cardiac output measurements employing several procedures, including the steps of (1) supplying power via an isolation transformer and carrier frequency to a catheter-mounted heating element; (2) measuring the voltage and current on the primary side of the isolation transformer; (3) determining the voltage and current on the secondary side of the transformer on the basis of the measured primary side voltage and current; and (4) calculating the power delivered to and resistance of the catheter-mounted heater on the basis of the secondary voltage and current. A heater power waveform generated with this process will be substantially free of electrical interference due to electrosurgical devices. Then, a system transfer function may be produced via signal processing techniques which involve cross-correlating the heater power waveform with the blood temperature waveform. The system transfer function will be uncorrupted, even if the blood temperature waveform contains moderate electrical interference, since the heater power waveform is free of any correlated electrical interference.

23 Claims, 2 Drawing Sheets

METHOD FOR REJECTING ELECTRICAL INTERFERENCE FROM PHYSIOLOGICAL MEASUREMENTS

BACKGROUND OF THE INVENTION

1. Field of the Invention

The present invention generally relates to the field of electronic noise rejection, and more particularly, relates to methods and apparatus for minimizing the effects of electromagnetic interference on physiological measurements.

2. Description of the Prior Art

Electronic monitors are currently used to measure various physiological parameters (e.g., blood pressure, heart rate, EKG, temperature) of patients during surgical procedures in the operating room (OR) and during care in intensive care units (ICUs). However, other electronic equipment in use in the OR or ICU (e.g., electrocautery or electrosurgical devices) can generate electrical interference which corrupts the measured signals and invalidates the displayed numeric readings and waveforms. Present monitors incorporate various means for minimizing this interference in EKG and blood pressure waveforms, but systems used to measure temperature and cardiac output remain susceptible to this type of interference.

A known method for performing cardiac output (CO) measurements employs heat and pulmonary artery catheters and relies upon the continuous measurement of pulmonary artery temperature and heater power to accurately compute cardiac output. For example, such a method is described by Yelderman in U.S. Pat. No. 4,507,974 and McKown et al. in U.S. patent application Ser. No. 510,897, filed Apr. 18, 1990. The delicate CO measurements made by such instruments must be free of corruption by electrical interference if these instruments are to be used reliably in the clinical setting. Unfortunately, since the most common source of electrical interference (electrocautery devices) can be used for prolonged periods of time and in an unpredictable fashion in the OR or ICU, the clinician cannot obtain reliable measurements at critical times without asking the surgeon to stop his or her procedure to allow the measurements to stabilize. Since time is of the essence in these procedures, interference of this type must be compensated or eliminated if the aforementioned CO measurement devices are to provide accurate measurements. The present invention has been provided to reject such electrical interference.

SUMMARY OF THE INVENTION

Accordingly, a primary object of the present invention is to provide methods and apparatus for minimizing the effects of electromagnetic or electrical interference on heat-based cardiac output measurements. A further object of the invention is to provide methods that are generally applicable to physiological signals that can be transferred across an isolation transformer. These and other objects are achieved by the present invention, which broadly encompasses methods and apparatus for obtaining a measurement of a parameter of interest while minimizing the effects of any electromagnetic noise on the measurement.

Methods and apparatus encompassed by the present invention comprise the steps of or means for: (a) injecting an indicator into a system for which a parameter of interest is to be measured, (b) measuring a first signal that is both indicative of the amount of the indicator injected in step (a) and substantially free of the effects of any electromagnetic interference, (c) determining on the basis of the first signal a first waveform representative of the amount of indicator delivered into the system as a function of time, where the first waveform is substantially free of the effects of the electromagnetic interference, (d) measuring a second signal that is indicative of a response of the system to the indicator, (e) determining on the basis of the second signal a second waveform representative of the response as a function of time, and (f) determining a system transfer function by cross-correlating the first waveform with the second waveform. The system transfer function will be both substantially uncorrupted by electromagnetic interference and indicative of the parameter of interest.

In one preferred embodiment of the invention, the system is a patient, the parameter of interest is a physiological parameter, and step (a) comprises supplying power to a catheter-mounted heating element associated with the patient. In specific applications, e.g., cardiac output measurement applications, step (a) may advantageously comprise supplying power to the heating element via an isolation transformer and a carrier frequency; step (b) may comprise measuring a voltage and a current on a primary side of the isolation transformer; and step (c) may comprise determining a voltage and current on a secondary side of the isolation transformer on the basis of the measured primary-side voltage and current, which step may include translating the primary-side voltage and current into a corresponding secondary-side voltage and current by using a model characterizing properties of the isolation transformer.

In addition, in cardiac output measurement contexts the indicator may advantageously be heat; step (c) may comprise calculating the power delivered to and resistance of the catheter-mounted heater on the basis of the secondary voltage and current; and the first waveform may be representative of the power delivered to the catheter-mounted heater. Further, the second signal may be indicative of the temperature of the patient's blood; the second waveform may be representative of the blood temperature as a function of time; and step (f) may comprise cross-correlating the heater power waveform with the blood temperature waveform.

Especially preferred embodiments of the present invention provide methods for substantially eliminating the effects of electrosurgical interference on continuous, heat-based cardiac output measurements. Such methods employ several procedures, including:

1. Supplying power via an isolation transformer and carrier frequency to the catheter-mounted heating element.

2. Measuring the voltage and current on the primary side of the isolation transformer.

3. Determining the voltage and current on the secondary side of the transformer on the basis of the measured primary side voltage and current. This may be accomplished by translating the primary voltage and current measurements into corresponding secondary measurements by using a mathematical model characterizing the transformer properties.

4. Calculating the power delivered to and resistance of the catheter-mounted heater on the basis of the secondary voltage and current. A heater power waveform generated with this process will be substantially free of electrical interference due to electrosurgical devices.

5. Producing a system transfer function via signal processing techniques, which involve cross-correlating the heater power waveform with the blood temperature waveform. The system transfer function will be uncorrupted, even if the blood temperature waveform contains moderate electrical interference, since the heater power waveform will be free of any correlated electrical interference.

Calibration of the transformer model can be achieved for a specific instrument by manually or electronically switching a known load resistance in place of the catheter circuit and performing a series of measurements. A calibration procedure in accordance with the present invention is described below in connection with the detailed description of preferred embodiments.

In addition, the uncorrupted voltage and current measurements derived with the transformer and transformer model may be used to provide a reliable measure of heater resistance, which may in turn be used to determine whether the heater is properly functioning.

BRIEF DESCRIPTION OF THE DRAWINGS

Other features and advantages of the invention will be appreciated to those skilled in the art from the following detailed description of which.

DETAILED DESCRIPTION OF PREFERRED EMBODIMENTS

A preferred embodiment of the present invention will now be described with respect to FIGS. 1-4 for use in a continuous cardiac output (CCO) monitor. However, those skilled in the art will appreciate that the description given herein is for exemplary purposes only and is not intended in any way to limit the scope of the invention. All questions regarding the scope of the invention may be resolved by referring to the appended claims.

In the preferred embodiment, the CCO monitor provides continuous cardiac output measurements using thermodilution-based techniques in conjunction with a pulmonary artery catheter. The catheter has a heating element of the type described, for example, by Yelderman et al. in U.S. patent application Ser. No. 07/647,578, filed Jan. 29, 1991, which is adapted to be placed in the region of the right atrium/ventricle of a patient. The heating element is powered by a pulsed (ON-OFF) signal and therefore sends a pulsed heat signal into the patient's blood. A thermistor near the catheter tip in the pulmonary artery senses the resultant blood temperature and these two signals are processed to provide CCO. See, e.g., Mark L. Yelderman, "Continuous Measurement of Cardiac Output With the Use of Stochastic System Identification Techniques", *J Clin Monit* 1990; 6(4):322-332.

The power delivered to the heating element must be accurately measured since this is indicative of the amount of indicator (heat) which is delivered into the blood. It is also necessary to accurately measure the resistance of the heating element, since this is used to estimate both the core and the surface temperatures of the heating element. These measurements are required for heater element monitoring and control algorithms. See Mark L. Yelderman, et al., "Thermal Safety of a Filamented Pulmonary Artery Catheter", *J Clin Monit*, (In Press 1992).

Figure 1:
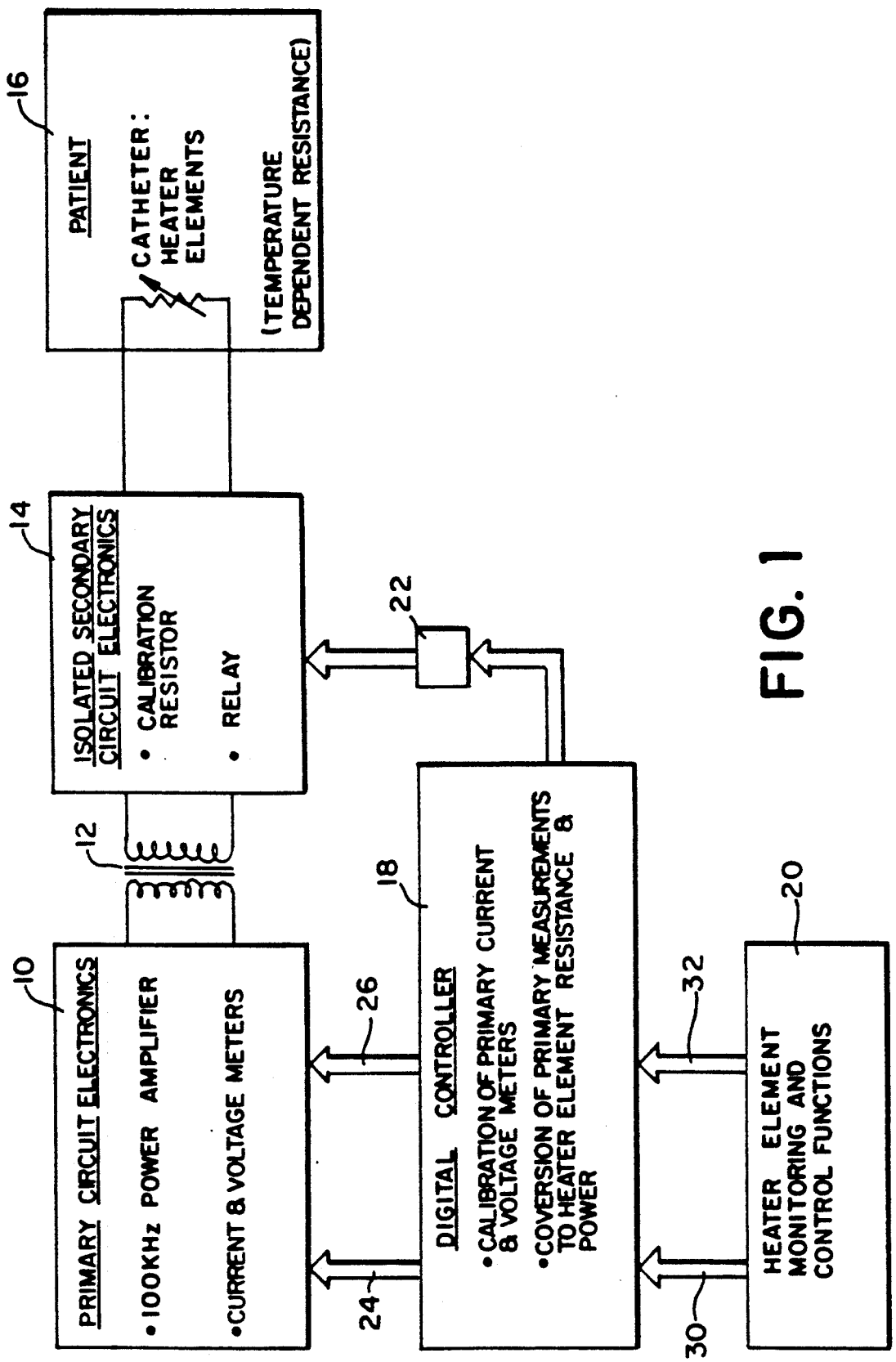
FIG. 1 is a block diagram of a system for delivering a heat indicator (e.g., for use in a cardiac output measurement system) in accordance with the present invention.

FIG. 1 is a block diagram of a system for delivering a heart indicator in accordance with the present invention. The system of FIG. 1 is embodied in the above-mentioned CCO monitor. In the system of FIG. 1, a primary-side electronics block 10 includes a 100 KHz power amplifier and current and voltage meters. The primary-side electronics block 10 is coupled to the primary side of an isolation transformer 12. The secondary side of the isolation transformer 12 is coupled to the secondary-side electronics block 14, which includes a calibration resistor and a relay. The secondary-side electronics block 14 is coupled to a catheter-mounted heater element that is adapted to be attached to a patient whose cardiac output is to be measured. The catheter-mounted heater element and patient are represented by block 16 in FIG. 1.

The primary-side electronics block 10 is further coupled to a digital controller block 18, which includes means (e.g., software) for calibration of the primary current and voltage meters (contained in the primary-side electronics block 10) and for conversion of primary-side measurements to heater element resistance and power measurements. The digital controller block 18 passes digital control data via a bus 26 to the primary-side electronics block 10, and receives current and voltage data, via another bus 24, from the primary-side electronics block. Digital controller block 18 is further coupled to a block 20 containing heater element monitoring and control functions. Block 20 provides digital control data to the digital controller block 18 via bus 32, and receives heater element power and resistance data via bus 30 from the digital controller block 18. The digital controller block 18 provides control signals, via relay control bus 28 and opto-isolator 22, to the secondary-side electronics block 14.

The IVM instrument acquires data that relates to the directly-measured electrical parameters of voltage (V) and current (I). Electrical power and resistance may be determined from V and I as:

$$P = I*V \text{ and } R = V/I.$$

However, the location of the voltage and current measurements are remote from the heater element, so it is necessary to analyze a small network to obtain the current and voltage of interest. Procedures for calibrating the current and voltage measurement systems and then using these measurements to estimate the heater element power and resistance are described below.

Non-ideal Isolation Transformer

In accordance with the present invention, an isolation transformer is employed to couple the power amplifier circuitry, which outputs a 100 KHz signal, to the heater element. The current and voltage measurement circuitry is placed on the primary side of the transformer to keep the circuitry to a minimum on the isolated secondary side. However, since the heater element is on the secondary side, it is necessary to relate the primary currents/voltages to the secondary currents/voltages.

Figure 2:
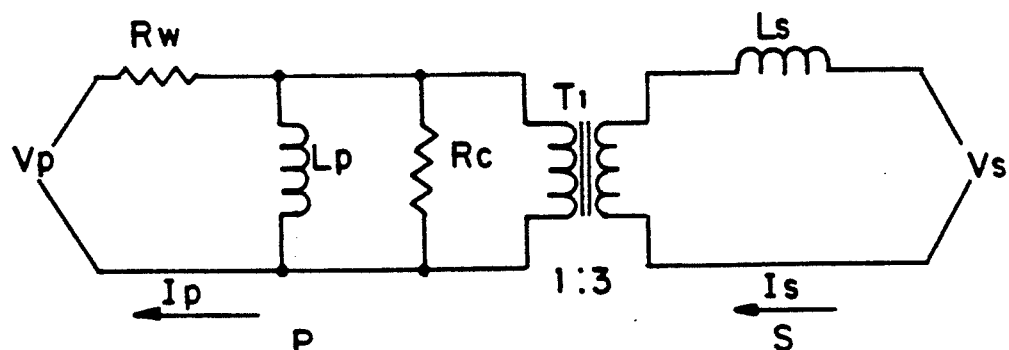
FIG. 2 is an electrical model of a non-ideal transformer that may be employed in practicing the present invention.
Figure 3:
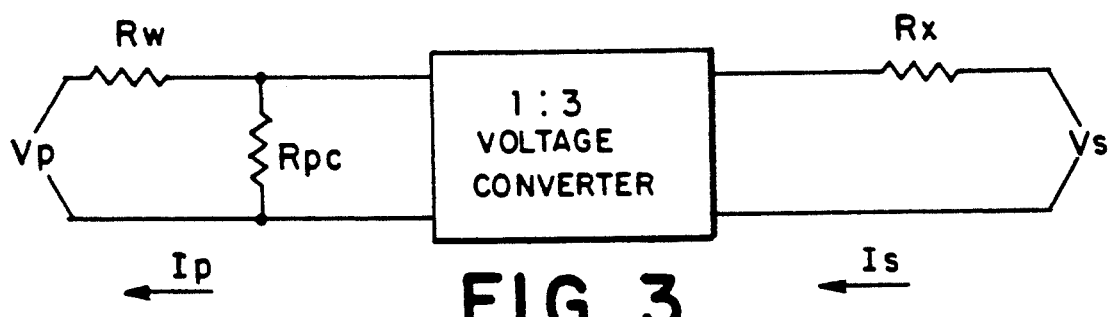
FIG. 3 is an RMS equivalent of the model of FIG. 2 for an operating frequency of 100 Khz.

For an ideal transformer with a primary-to-secondary turns ratio of 1:N, the root-mean-squared (RMS) voltages and currents relate simply as:

$$V_s = N * V_p$$

$$I_s = I_p / N$$

where the s/p subscript represents secondary/primary. For a non-ideal transformer (i.e., a more realistic model), the primary and secondary relationships depend upon additional electrical circuit parameters. It has been experimentally determined that the assumption of an ideal transformer is inconsistent with the required measurement accuracies, therefore a more realistic circuit model of the isolation transformer has been obtained. FIG. 2 is a model of a non-ideal transformer. The circuit components are:

Rw = effective primary resistance of the wire (=0.08 Ω)
Rc = effective resistance due to core losses (see below),
Lp = effective primary shunt inductance (=220 μH),
Ls = effective secondary series inductance (= 2 μH).

The effective core loss resistance Rc in the exemplary CCO monitor is a linear function of the primary voltage according to the equation:

$$Rc = m\_Rc * V_p + b\_Rc \qquad (1)$$

where m_Rc = 22.8 ohms/volts and b_Rc = 445 ohms. The analysis here is simplified because: (1) the signal is a 100 KHz sinewave, and (2) the current and voltage for this circuit and this frequency have a negligible phase lag. This allows the RMS equivalent DC circuit of FIG. 3 to be used.

Figure 4:
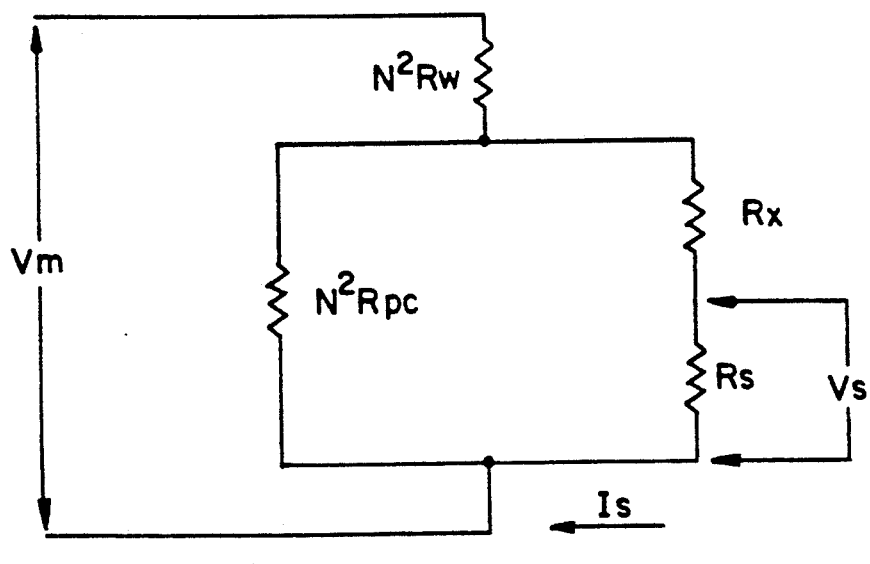
FIG. 4 depicts an image of the secondary of the RMS equivalent model of FIG. 3.

In accordance with the present invention, the primary current and voltage measurement hardware/software is calibrated in terms of the secondary current and voltage values; for this purpose the simple resistor network of FIG. 4 (which "images" the primary circuit onto the secondary in accordance with the transformer turns ratio) may be analyzed. Well known network analysis techniques such as current summation and voltage drops provide the following equations:

$$Vm = Vs*(1 + Rw/Rpc) + Is*[N^2*Rw + Rx*(1 + Rw/Rpc)] \qquad (2)$$

$$Im = Vs/(N^2*Rpc) + Is[1 + Rx/(N^2*Rpc)]$$

where:
Rs represents the secondary load resistance (ohms),
Vm = measured RMS voltage (volts),
Im = measured RMS current (amps),
Rpc = Rp*Rc/(Rp+Rc) (ohms),
Rp = "resistance" of Lp at 100 KHz (= 1000 ohms),
Rx = "resistance" of Ls at 100 KHz (= 1.0 ohms),
N = secondary-to-primary transformer turns ratio (= 3).

The secondary voltage and current are given by:

$$Vs = Vm*(1 + Rx/(N^2*Rpc)) - Im*[N^2*Rw+Rx*(1+Rw/Rpc)] \qquad (3)$$

$$Is = -Vm/(N^2*Rpc) + Im*(1 + Rw/Rpc)$$

Voltage and Current Meter Calibration

The CCO monitor includes a relay on the output of the isolation transformer that can switch between the external catheter cable/heating element and an internal calibration resistor, R_cal. The hardware calibration of the monitor includes a reference level adjustment on the 100 KHz power signal. The DAC-controlled voltage source that drives the primary of the isolation transformer is set such that a DAC value of 220 provides a reference voltage of 23.53 volts across the calibration resistor R_cal (= 39.0 ohms, within +/− 1%, in one embodiment of the invention). This reference voltage is used to calibrate the primary RMS current and voltage measurement circuits during the initial entry into CCO mode and after every 12 hours of CCO operation.

The runtime software-controlled calibration procedure is as follows:

1. the relay is switched to the calibration resistor;
2. the DAC is set to 220 and the power amps are activated (thus 23.53 V is placed across R_cal);
3. the software controlled gain potentiometers are adjusted in the current and voltage meter circuits such that the digitized values, ADC_v and ADC_i are closest to ADC_v_cal (= 3446) and ADC_i_cal 3446);
4. the DAC is set to 110, 160 and 220 and the values ADC_V(DAC) and ADC_i(DAC) are recorded;
5. VS(DAC) is computed for DAC = 110, 160 and 220 using the equation:

$$VS(DAC) = m\_DAC * DAC + b\_DAC \text{ (volts)}$$

where m_DAC (= 0.1059) and b_DAC (= 0.2327) represent constants for the specific hardware employed (the values given are for one embodiment of the invention);

6. equation (1) is used with the equation:

$$Vp = [Vs(DAC)*(R\_cal + N^2*Rw + Rx)/R\_cal)]/N$$

to compute RC(DAC) for 110, 160 and 220;

7. equations (2) are used with the equation:

$$IS(DAC) = Vs(DAC)/R\_cal \text{ (amps)}$$

to provide the desired measurement levels, VM(DAC) and IM(DAC) for DAC =110, 160, 220;

8. the data sets Vm (DAC) versus ADC_v (DAC) are fit to a line (e.g., using a least squares algorithm) to provide the calibration parameters, m_Vm_cal and b_Vm_cal such that:

$$Vm = m\_Vm\_cal * ADC\_v + b\_Vm\_cal \text{ (volts)}; \qquad (4)$$

9. the data sets Im (DAC) versus ADC_i (DAC) are fit to a least squares line to provide the calibration parameter, m_Im_cal and b_im_cal such that:

$$Im = m\_Im\_cal \cdot ADC\_i + b\_Im\_cal (amps). \qquad (5)$$

After this procedure, the meter circuits will be calibrated such that equation (4) will provide N times the actual primary voltage (where N = 3 in the present example), given ADC_v, and equation (5) provides 1/N times the actual primary current, given ADC_i.

Heater Element Resistance and Power Measurement

During CCO data acquisition, the output relay switches so that the secondary load is:

$$Rs = R\_loss + R\_he$$

where $R\_he$ represents the RMS equivalent resistance of the heater element and $R\_loss$ represents the series resistance from the secondary terminals of the transformer to the heater element. Note that, since $R\_loss$ is a function of catheter/heater element design, it may be programmed into a catheter EEPROM of the type described by Yelderman et al. in U.S. patent application Ser. No. 07/769,536, filed Oct. 1, 1991. In one embodiment of the heater Reloss is 2.25 ohms and $R\_he$ ranges from 35 to 45 ohms.

The following procedure allows the quantities of interest, i.e., the heater element resistance $R\_he$ and power $P\_he$, to be extracted from the primary-based current and voltage measurements, $I\_m$ and $V\_m$:

1. obtain the measured current and voltage, Im and Vm;
2. use equation (1) with:

$$Vp = [m\_Vm\_cal * ADC\_v + b\_Vm\_cal] / N$$

to compute Rc for the current DAC setting;

3. use equation (3) to compute the secondary current and voltage (Is and Vs);
4. relate Is and Vs to the heater element current and voltage ($I\_he$, $V\_he$), i.e., $$I\_he = Is$$

$$V\_he = (R\_he/(R\_loss + R\_he) * Vs;$$

5. compute the heater element resistance and power, $$R\_he = V\_he/I\_he$$

$$P\_he = V\_he*I\_he.$$

The above procedure is performed on a sample-by-sample basis in preferred embodiments of the invention. $R\_he$ and $P\_he$ are input to the heater element monitoring and control algorithms. $P\_he$ is also input to a CCO estimation algorithm as described in the above-cited U.S. patent application Ser. No. 07/510,897.

Heater Element Resistance calibration

To achieve a desired accuracy in the absolute resistance measurement (e.g., +/- 0.1 ohm), the CCO monitor includes a resistance adjustment resistor ($R\_adj$) placed in parallel with the catheter's heater element. The $R\_adj$ resistance includes a ten-turn 100K$\Omega$ potentiometer in series with a 10K$\Omega$ fixed resistor (to protect against 0 ohms on the ten-turn potentiometer). $R\_adj$ has been safely ignored in the above discussions due to the fact that:

$$R\_loss + R\_he < 45 \text{ ohs} << R\_adj \text{ (approx. 60 K}\Omega\text{)}.$$

Including $R\_adj$ gives rise to negligible terms in the network equations.

In accordance with the present invention, the monitor undergoes the following resistance calibration procedure:

1. "Power ROM" calibration software is placed in the unit to provide an interface to the relevant calibration and data acquisition software;
2. the monitor's cable is connected to a special resistance test box which contains known fixed resistors and a special EEPROM with an $R\_loss = 0.5$ ohms (resistance from transformer's secondary to the end of the patient cable);
3. the heater element power output circuits are continuously activated at a requested power, e.g., 15 watts (see below);
4. the computed values for heater element resistance, $R\_he$, are monitored and the $R\_adj$ potentiometer is adjusted until the $R\_he$ measurements agree with the known test resistance to within, e.g., +/- 0.02 ohms.

Requested Power Algorithm

The following procedure is executed whenever it is necessary to determine a DAC setting given a requested power of $P\_req$ watts and an anticipated core temperature of $T\_core$ degrees centigrade:

1. compute the anticipated heater element resistance using the Ro, To, and TCR parameters, i.e., $R\_he = Ro*[(T\_core - To)*TCR + 1[$, where Ro represents the reference resistance of the heater element at reference temperature To and TCR represents the temperature coefficient of is resistance (1/°C.);
2. compute the voltage drop across the heater element as:

$$V\_he = (P\_req * R\_he)^{\frac{1}{2}};$$

3. compute the voltage across the secondary of the isolation transformer as:

$$Vs = ((0.5 + R\_he)/R\_he) * V\_he;$$

4. compute the DAC setting as:

$$DAC = (Vs-b\_DAC)/m\_DAC,$$

where $b\_DAC$ and $m\_DAC$ are the constants discussed above.

It has been observed that this procedure typically provides a measured power within +/- 3% of the requested power ($P\_req$). This variance depends upon the agreement between the anticipated and the realized core temperatures, which is flow dependent. However, it is only the accuracy of the measured power (which is within +/- 1%) that has any substantial effect on the accuracy of the CCO measurement or heater monitor and control functions.

Finally, many modifications of the specific methods and apparatus described in this specification will fall within the true scope of the invention as described in the following claims. For example, the present invention is not limited to applications in systems for measuring cardiac output, since it is apparent that the invention may be advantageously applied in other kinds of electronic systems that suffer from electromagnetic noise. In addition, approaches other than use of an isolation transformer may be used to produce one uncorrupted signal for use in a cross-correlation operation with a second corrupted signal. For example, for certain types of interference which create "glitches" on a temperature waveform, a software routine may be applied to the corrupted temperature data to generate an uncorrupted waveform which may then be used together with a second waveform (e.g., a corrupted heater power waveform) to produce an uncorrupted system transfer function which can be used to measure cardiac output. Furthermore, the scope of protection of the following claims is not intended to be limited to the particular exemplary hardware and software elements described above.

What is claimed is:

1. A method for obtaining a measurement of a parameter of interest of a system while minimizing the effects of any electromagnetic interference on said measurement, comprising the steps of:
   (a) injecting an amount of indicator into said system by supplying power to said system via an isolation transformer and a carrier frequency;
   (b) measuring a first signal that is both indicative of said amount of said indicator injected in step (a) and substantially free of the effects of said electromagnetic interference;
   (c) determining, from said first signal, a first waveform representative of said amount of said indicator delivered into said system as a function of time, said first waveform being substantially free of the effects of said electromagnetic interference;
   (d) measuring a second signal that is indicative of a response of said system to said indicator;
   (e) determining, from said second signal, a second waveform representative of said response as a function of time; and
   (f) determining a system transfer function by cross-correlating said first waveform with said second waveform, said system transfer function being both substantially uncorrupted by said electromagnetic interference and indicative of said parameter of interest.

2. The method recited in claim 1, wherein said system is a patient, said parameter of interest is a physiological parameter, and step (a) comprises the steps of inserting a catheter-mounted heating element into the patient and supplying power to said catheter-mounted heating element via said isolation transformer and said carrier frequency.

3. The method recited in claim 2, wherein step (b) comprises the step of measuring a first voltage and a first current on a primary side of said isolation transformer.

4. The method recited in claim 3, wherein step (c) comprises the step of determining a second voltage and a second current on a secondary side of said isolation transformer from said measured first voltage and said first current.

5. The method recited in claim 4, wherein step (c) comprises the further step of translating said first voltage and said first current into said second voltage and said second current by using a model characterizing properties of said isolation transformer.

6. The method recited in claim 4, wherein said indicator is heat and the patient's blood is heated by said heating element, step (c) comprises the step of calculating the power delivered to and resistance of said catheter-mounted heating element from said second voltage and said second current, and said first waveform is representative of the power delivered to said catheter-mounted heating element.

7. The method recited in claim 6, wherein said system response is the patient's blood temperature and said second signal is indicative of said blood temperature, said second waveform is representative of said blood temperature as a function of time, and step (f) comprises the step of cross-correlating said first waveform with said second waveform.

8. The method recited in claim 1, wherein step (b) comprises the step of measuring a first voltage and a first current on a primary side of said isolation transformer.

9. The method recited in claim 8, wherein step (c) comprises the step of determining a second voltage and a second current on a secondary side of said isolation transformer from said measured first voltage and said first current.

10. The method recited in claim 9, wherein step (c) comprises the further step of translating said first voltage and said first current into said second voltage and said second current by using a model characterizing properties of said isolation transformer.

11. A method for substantially eliminating the effects of electrosurgical interference on continuous, heat-based cardiac output (CO) measurements, comprising:
    (a) supplying power via an isolation transformer and carrier frequency to a catheter-mounted heating element inserted into a patient for whom a CO measurement is to be obtained;
    (b) measuring a first voltage and a first current on a primary side of said isolation transformer;
    (c) determining a second voltage and a second current on a secondary side of said transformer from the measured first voltage and first current;
    (d) determining the power delivered to and resistance of said catheter-mounted heating element from the second voltage and the second current;
    (e) determining a heater power waveform from said power delivered to and resistance of said catheter-mounted heating element, said heater power waveform being substantially free of electrical interference due to electrosurgical devices;
    (f) obtaining a blood temperature waveform that is representative of a temperature associated with the blood of said patient and indicative of a response of said patient to said power delivered to said heating element; and
    (g) producing a system transfer function via signal processing techniques that include cross-correlating said heater power waveform with said blood temperature waveform, said system transfer function being substantially uncorrupted by electrical interference.

12. The method recited in claim 11, comprising the further step of determining the CO measurement for said patient from at least said system transfer function.

13. The method recited in claim 12, wherein said transformer has certain properties, and step (c) comprises the step of translating the primary-side voltage and current measurements into corresponding secondary-side measurements by using a mathematical model characterizing said properties of said transformer.

14. An apparatus for obtaining a measurement of a parameter of interest of a system while minimizing the effects of any electromagnetic interference on said measurement, comprising:
    (a) first means for injecting an indicator into said system comprising means for supplying power to said system via an isolation transformer and a carrier frequency;
    (b) second means for measuring a first signal that is both indicative of an amount of said indicator injected by said first means and substantially free of the effects of said electromagnetic interference;

(c) third means for determining, from said first signal, a first waveform representative of the amount of said indicator delivered into the patient as a first function of time, said first waveform being substantially free of the effects of the electromagnetic interference;

(d) fourth means for measuring a second signal that is indicative of a response of the patient to said indicator;

(e) fifth means for determining, from said second signal, a second waveform representative of said response as a second function of time; and (f) sixth means for determining a system transfer function by cross-correlating said first waveform with said second waveform, said system transfer function being both substantially uncorrupted by said electromagnetic interference and indicative of said physiological parameter.

15. The apparatus recited in claim 14, wherein said system is a patient, said parameter of interest is a physiological parameter, and said first means further comprises a catheter-mounted heating element inserted into said patient and means for supplying power to said heating element via said isolation transformer and said carrier frequency.

16. The apparatus recited in claim 15, wherein said second means comprises means for measuring a first voltage and a first current on a primary side of said isolation transformer.

17. The apparatus recited in claim 16, comprising means for determining a second voltage and a second current measurement on a secondary side of said isolation transformer from said first voltage and said first current measurement.

18. The apparatus recited in claim 17, comprising means for translating said first voltage and said first current measurement into said second voltage and said second current by using a model characterizing properties of said isolation transformer.

19. The apparatus recited in claim 17, wherein said indicator is heat, and comprising means for calculating the power delivered to and resistance of said catheter-mounted heating element from said second voltage and said second current measurements, said first waveform being representative of the power delivered to said catheter-mounted heating element.

20. The apparatus recited in claim 19, wherein said second signal is indicative of the temperature of patient's blood, said second waveform is representative of said blood temperature as a function of time, and said sixth means comprises means for cross-correlating said first waveform with said second waveform.

21. The apparatus recited in claim 14, wherein said second means comprises means for measuring a first voltage and a first current on a primary side of said isolation transformer.

22. The apparatus recited in claim 21, comprising means for determining a second voltage and a second current measurement on a secondary side of said isolation transformer from said first voltage and said first current measurement.

23. The apparatus recited in claim 22, comprising means for translating said first voltage and said first current measurement into said second voltage and said second current by using a model characterizing properties of said isolation transformer.

* * * * *